(12) United States Patent
Gallant

(10) Patent No.: US 7,174,678 B2
(45) Date of Patent: Feb. 13, 2007

(54) MODULAR PATIENT ROOM

(75) Inventor: Dennis J. Gallant, Harrison, OH (US)

(73) Assignee: Hill-Rom Services, Inc., Wilmington, DE (US)

(*) Notice: Subject to any disclaimer, the term of this patent is extended or adjusted under 35 U.S.C. 154(b) by 906 days.

(21) Appl. No.: 10/071,361

(22) Filed: Feb. 8, 2002

(65) Prior Publication Data
US 2002/0104271 A1    Aug. 8, 2002

Related U.S. Application Data

(63) Continuation-in-part of application No. 09/298,257, filed on Apr. 22, 1999, now Pat. No. 6,405,491.

(60) Provisional application No. 60/293,949, filed on May 25, 2001.

(51) Int. Cl.
E04B 2/74 (2006.01)
E04H 3/08 (2006.01)

(52) U.S. Cl. ............... 52/36.1; 52/36.4; 52/34; 52/220.1; 52/220.2; 52/64

(58) Field of Classification Search ........ 52/36.1–36.5, 52/79.1, 79.5, 34, 220.1–220.2, 220.3, 220.7, 52/238.1, 64–72, 110, 111
See application file for complete search history.

(56) References Cited

U.S. PATENT DOCUMENTS

| | | | |
|---|---|---|---|
| 580,326 A * | 4/1897 | McCallum | 101/208 |
| 1,966,800 A * | 7/1934 | Katzman | 312/225 |
| 2,027,491 A * | 1/1936 | Walter | 108/42 |
| 2,739,785 A | 3/1956 | Gray | |
| 2,834,030 A | 5/1958 | Jones | |
| 2,894,794 A | 7/1959 | Mays | |
| 3,115,819 A | 12/1963 | Mahimeister et al. | |
| 3,241,850 A | 3/1966 | Propst | |
| 3,250,583 A | 5/1966 | Phillips | |
| 3,267,955 A | 8/1966 | Logan et al. | |
| 3,294,480 A | 12/1966 | Potapenko | |
| 3,362,704 A | 1/1968 | Pilz | |
| 3,378,963 A | 4/1968 | Obata | |
| 3,462,920 A | 8/1969 | Denny | |
| 3,514,794 A | 6/1970 | Pofferi | |
| 3,601,031 A | 8/1971 | Abel et al. | |
| 3,660,591 A | 5/1972 | Schultz et al. | |
| 3,694,830 A | 10/1972 | Koller | |

(Continued)

FOREIGN PATENT DOCUMENTS

DE        570079        2/1933

(Continued)

OTHER PUBLICATIONS

Hill-Rom Future of Care 4.0 Videotape, 1999, Copyright Hill-Rom Company, Inc.

*Primary Examiner*—Jeanette Chapman
(74) *Attorney, Agent, or Firm*—Barnes & Thornburg LLP

(57) ABSTRACT

A modular patient room includes a plurality of modular wall panels or units having various configurations. In some embodiments, the modular wall units have water dispensers. Headwall units having water dispensers are also disclosed. The water dispensers are configured to filter water or to sterilize water.

18 Claims, 11 Drawing Sheets

U.S. PATENT DOCUMENTS

| | | | | |
|---|---|---|---|---|
| 3,727,753 | A | 4/1973 | Starr et al. | |
| 3,742,932 | A | 7/1973 | Greenspan | |
| 3,774,522 | A | 11/1973 | Marsh | |
| 3,829,906 | A | 8/1974 | McPhee | |
| 3,846,853 | A | 11/1974 | Jacobsson | |
| 3,921,345 | A | 11/1975 | Damico | |
| 3,975,271 | A | 8/1976 | Saunier et al. | |
| 4,043,932 | A | 8/1977 | Fresenius et al. | |
| 4,072,157 | A | 2/1978 | Wines, Jr. et al. | |
| 4,104,710 | A | 8/1978 | Damico et al. | |
| 4,129,122 | A | 12/1978 | Dout et al. | |
| 4,202,676 | A | 5/1980 | Pelosi, Jr. et al. | |
| 4,267,769 | A | 5/1981 | Davis et al. | |
| 4,338,485 | A | 7/1982 | Fullenkamp et al. | |
| 4,342,651 | A | 8/1982 | Ahrens | |
| 4,359,843 | A | 11/1982 | Schachar | |
| 4,360,991 | A | 11/1982 | West | |
| 4,409,889 | A | 10/1983 | Burleson | |
| 4,451,341 | A | 5/1984 | Miller | |
| 4,475,322 | A | 10/1984 | Russo et al. | |
| 4,506,595 | A | 3/1985 | Roberts et al. | |
| 4,535,247 | A | 8/1985 | Kurtz | |
| 4,569,163 | A | 2/1986 | Long | |
| 4,586,759 | A | 5/1986 | Wrobel | |
| 4,589,557 | A * | 5/1986 | Bollmann | 211/94.01 |
| 4,594,154 | A | 6/1986 | Bissardon et al. | |
| 4,612,679 | A | 9/1986 | Mitchell | |
| 4,615,799 | A | 10/1986 | Mortensen | |
| 4,646,211 | A | 2/1987 | Gallant et al. | |
| 4,667,579 | A | 5/1987 | Daw | |
| 4,753,055 | A | 6/1988 | Durham, Jr. | |
| 4,755,292 | A | 7/1988 | Merriam | |
| 4,761,208 | A | 8/1988 | Gram et al. | |
| 4,821,470 | A | 4/1989 | Kappers et al. | |
| 4,850,268 | A | 7/1989 | Saito et al. | |
| 4,857,204 | A | 8/1989 | Joklik | |
| 4,946,574 | A | 8/1990 | Lin | |
| 4,978,297 | A | 12/1990 | Vlock | |
| 5,060,425 | A * | 10/1991 | Kappers et al. | 52/36.4 |
| 5,065,462 | A | 11/1991 | Romano | |
| 5,068,030 | A | 11/1991 | Chen | |
| 5,074,894 | A | 12/1991 | Nelson | |
| 5,086,593 | A | 2/1992 | Walentine | |
| 5,097,550 | A | 3/1992 | Marra, Jr. | |
| 5,107,636 | A | 4/1992 | Schindele et al. | |
| 5,108,063 | A | 4/1992 | Koerber, Sr. et al. | |
| 5,147,605 | A | 9/1992 | Tatsuno et al. | |
| 5,152,814 | A | 10/1992 | Nelson | |
| 5,158,454 | A | 10/1992 | Viebahn et al. | |
| 5,174,285 | A | 12/1992 | Fontenot | |
| 5,212,915 | A | 5/1993 | Antonio | |
| 5,247,962 | A | 9/1993 | Walker | |
| 5,256,105 | A | 10/1993 | Austin | |
| 5,273,713 | A | 12/1993 | Levy | |
| 5,304,213 | A | 4/1994 | Berke et al. | |
| 5,314,243 | A | 5/1994 | McDonald et al. | |
| 5,319,816 | A | 6/1994 | Ruehl | |
| 5,323,565 | A * | 6/1994 | Kappers et al. | 52/36.4 |
| 5,337,525 | A * | 8/1994 | Zaccai et al. | 52/35 |
| 5,359,820 | A | 11/1994 | McKay | |
| 5,384,032 | A | 1/1995 | de Souza | |
| 5,395,492 | A | 3/1995 | Schoeberl | |
| 5,425,793 | A | 6/1995 | Mori et al. | |
| 5,439,576 | A | 8/1995 | Schoeberl | |
| RE35,035 | E | 9/1995 | Shipley | |
| 5,447,640 | A | 9/1995 | Omi et al. | |
| 5,448,859 | A | 9/1995 | Walker et al. | |
| 5,487,814 | A | 1/1996 | Santasalo | |
| 5,507,734 | A | 4/1996 | Everett, Jr. et al. | |
| 5,555,582 | A | 9/1996 | Jerideau | |
| 5,556,279 | A | 9/1996 | Wolf et al. | |
| 5,561,412 | A | 10/1996 | Novak et al. | |
| 5,573,666 | A | 11/1996 | Korin | |
| 5,622,622 | A | 4/1997 | Johnson | |
| 5,623,948 | A | 4/1997 | Van Morris | |
| 5,653,064 | A * | 8/1997 | Kappers et al. | 52/36.4 |
| 5,699,038 | A | 12/1997 | Ulrich et al. | |
| 5,707,125 | A * | 1/1998 | Coglin | 312/242 |
| 5,756,933 | A | 5/1998 | Pitchford et al. | |
| 5,838,223 | A | 11/1998 | Gallant et al. | |
| 5,851,388 | A | 12/1998 | Suh | |
| 5,852,904 | A * | 12/1998 | Yu et al. | 52/220.7 |
| 5,878,536 | A * | 3/1999 | Demmitt et al. | 52/36.4 |
| 5,890,326 | A | 4/1999 | Gallant et al. | |
| 5,897,757 | A | 4/1999 | Sano | |
| 5,903,937 | A | 5/1999 | Clarke | |
| 5,970,663 | A * | 10/1999 | McDonough | 52/36.4 |
| 6,006,379 | A | 12/1999 | Hensley | |
| 6,059,965 | A | 5/2000 | Laing et al. | |
| 6,071,473 | A | 6/2000 | Darwin | |
| 6,145,253 | A * | 11/2000 | Gallant et al. | 52/36.1 |
| 6,147,592 | A | 11/2000 | Ulrich et al. | |
| 6,161,347 | A * | 12/2000 | Yu et al. | 52/220.7 |
| 6,193,894 | B1 | 2/2001 | Hollander | |
| 6,213,481 | B1 | 4/2001 | Marchese et al. | |
| 6,220,681 | B1 | 4/2001 | Swensson et al. | |
| 6,235,191 | B1 | 5/2001 | Nakamura | |
| 6,243,993 | B1 | 6/2001 | Swensson | |
| 6,256,936 | B1 | 7/2001 | Swensson et al. | |
| 6,344,794 | B1 | 2/2002 | Ulrich et al. | |
| 6,405,491 | B1 * | 6/2002 | Gallant | 52/36.1 |
| 6,748,710 | B2 * | 6/2004 | Gresham et al. | 52/242 |
| 6,807,776 | B2 * | 10/2004 | Girdwood et al. | 52/36.1 |
| 6,920,727 | B2 * | 7/2005 | Yu et al. | 52/239 |

FOREIGN PATENT DOCUMENTS

| | | |
|---|---|---|
| DE | 836236 | 4/1952 |
| DE | 1930789 | 12/1970 |
| DE | 2204573 | 8/1973 |
| DE | 2228898 | 1/1974 |
| DE | 2544221 | 12/1976 |
| DE | 8434471 | 5/1985 |
| DE | 3541017 | 6/1986 |
| DE | 9204321 | 5/1992 |
| DE | 4228873 | 10/1993 |
| DE | 4416618 | 7/1995 |
| DE | 4409069 | 9/1995 |
| DE | 29720195 | 1/1998 |
| DE | 19750478 | 6/1999 |
| DE | 29923051 | 4/2000 |
| DE | 200 18 317 U1 | 2/2001 |
| EP | 0 311 336 | 4/1989 |
| EP | 0 481 942 A1 | 4/1992 |
| EP | 0947187 | 10/1999 |
| EP | 0 966 944 A2 | 12/1999 |
| EP | 0 969 241 A1 | 1/2000 |
| EP | 1030143 | 8/2000 |
| FR | 2213070 | 8/1974 |
| GB | 1 490 381 | 11/1977 |
| JP | 05280125 A * | 10/1993 |
| WO | WO 94/20784 | 9/1994 |
| WO | WO 98/33419 | 8/1998 |
| WO | WO 98/50840 | 11/1998 |
| WO | WO 01/33529 | 5/2001 |

* cited by examiner

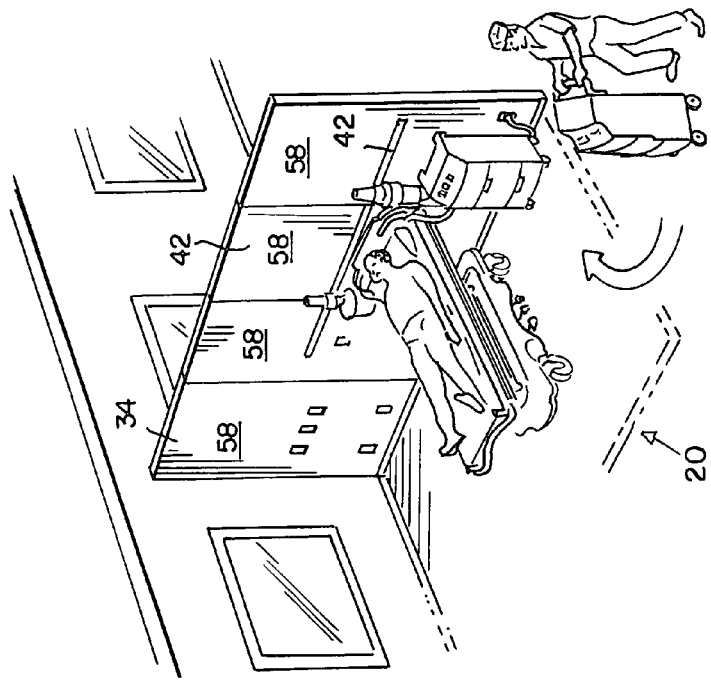
FIG. 4
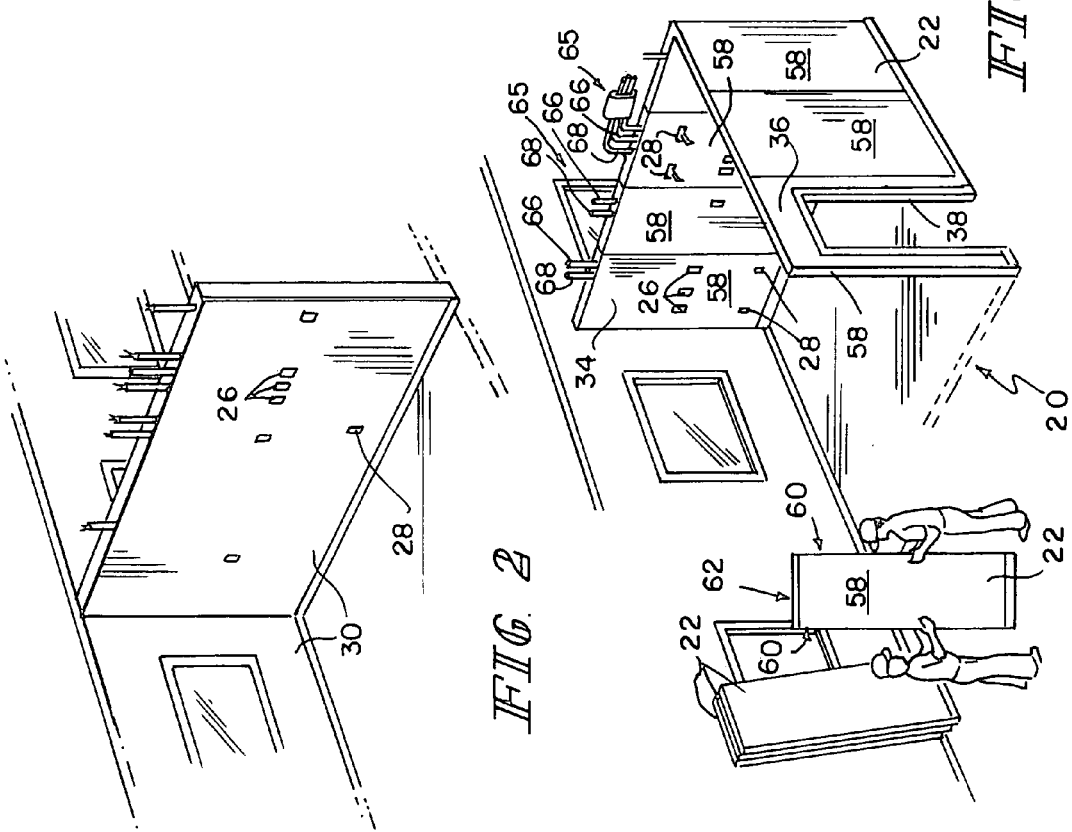
FIG. 2
FIG. 3

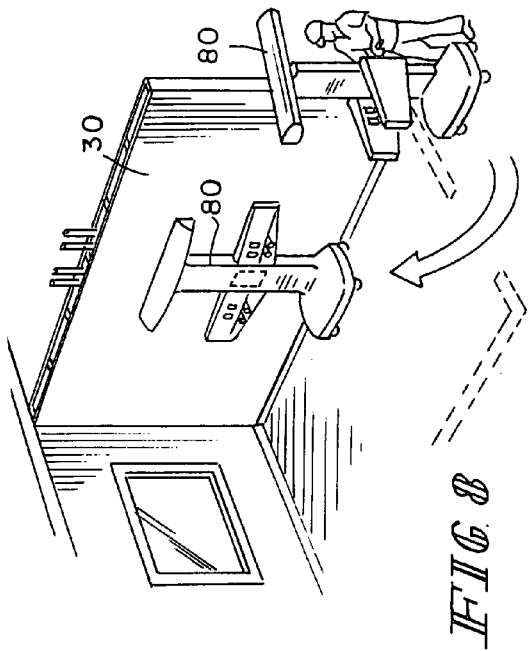
FIG. 8
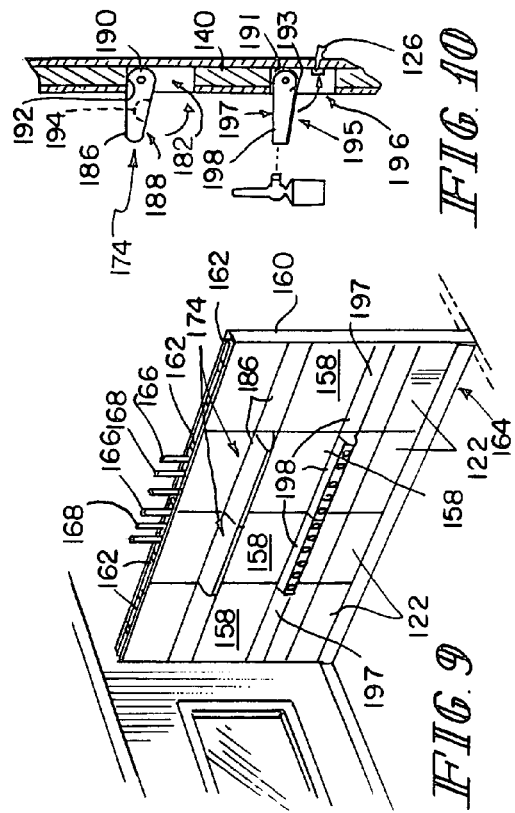
FIG. 9
FIG. 10
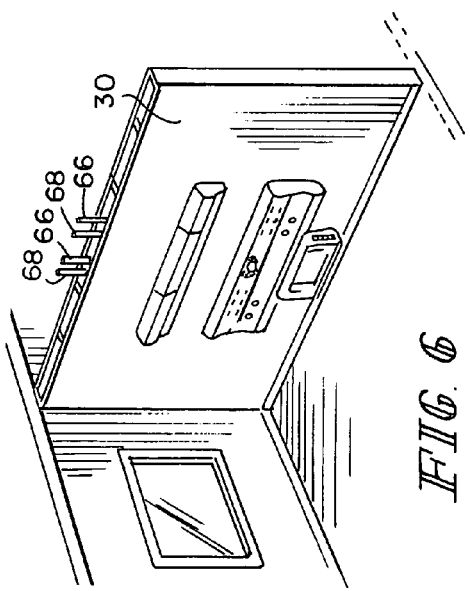
FIG. 6
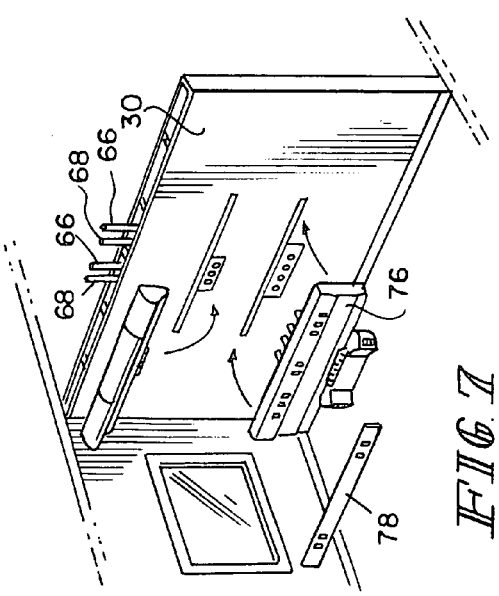
FIG. 7

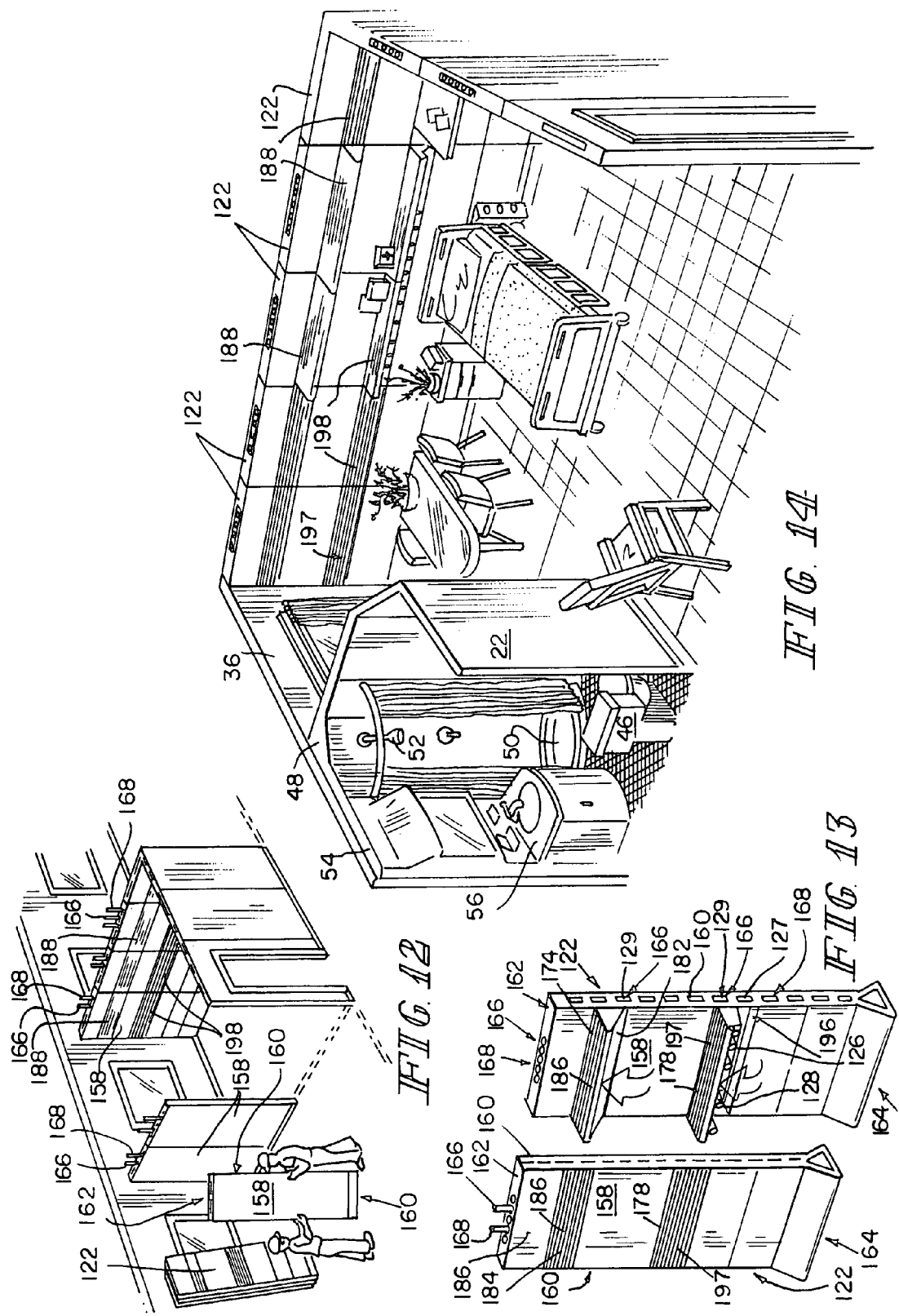

US 7,174,678 B2

MODULAR PATIENT ROOM

This application is a continuation-in-part of U.S. patent application Ser. No. 09/298,257 which was filed Apr. 22, 1999 now U.S. Pat. No. 6,405,491 and which is hereby incorporated by reference herein. This application also claims priority under 35 U.S.C. § 119(e) to U.S. Provisional Patent Application Ser. No. 60/293,949 which was filed on May 25, 2001 and which is hereby incorporated by reference herein.

BACKGROUND AND SUMMARY

The present disclosure relates to adaptable clinical environments and particularly, to modular components for installation into a clinical environment. More particularly, the present disclosure relates to modular panels or units having patient-care components or service-delivery components coupled thereto.

Modular components for dividing open spaces into cubicles and rooms are well known.

A modular patient room for installation in a healthcare facility having gas supply lines, electrical supply lines, and water supply lines in accordance with one aspect of the present disclosure includes wall panels having oppositely facing spaced apart wall surfaces, oppositely facing spaced apart side walls configured for joining to the side wall of another wall panel, a top surface, a bottom surface, and an interior. One of the wall panels includes a conduit having a first end extending through a wall surface of the wall panel and a second end separated from the first end by an internal portion disposed in the interior of wall panel, the second end extending through one of the sidewalls, top surface, and bottom surface and being configured for connection to one of the gas, electrical and water supply lines. The modular patient room may also include couplings in the side walls connected to the second end of the conduit, the couplings being designed and arranged to couple conduits of abutting wall panels. Also a cavity may be formed in the wall surface so that the first end of conduit can extend through cavity of wall surface, and a panel may be pivotally attached to wall surface to pivot between a first position in which first end of conduit is concealed and a second position in which first end of conduit is accessible. The conduit may be gas piping or electrical wiring.

A modular system for use in a healthcare facility in accordance with one aspect of the present disclosure includes a plurality of wall panels having side walls and a unit having edge walls and also having water supply and waste water conduits formed therein for connection to a water-using device. The edge walls of the unit and the side walls of the wall panels include connectors configured to join to connectors of other wall panels and units. The unit may be a shower, a toilet, or a sink.

According to another aspect of this disclosure, an apparatus for use in a healthcare facility to dispense water to a point of care in the healthcare facility is provided. The apparatus comprises a headwall unit mounted to a wall of the healthcare facility. The headwall unit has a gas outlet through which gas is delivered. The apparatus further comprises a water dispenser coupled to the headwall unit. The water dispenser is coupled to a water line of the healthcare facility and the water dispenser is operable to dispense water to the point of care. In some embodiments, the water dispenser filters the water, and in other embodiments, the water dispenser sterilizes the water. Alternatively, the water dispenser is coupled to a modular wall unit.

Additional features and advantages of the present invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures, in which:

FIG. 2 is a perspective view of a conventional wall wired and plumbed for receipt of modular patient service equipment;

FIG. 3 is a perspective view of a partially assembled patient room showing a conventional wall, two walls constructed from wall panels, and free standing wall panels which will be assembled by workers to form the fourth wall of a patient room;

FIG. 4 is a perspective view of a patient room with two walls removed for clarity showing a conventional wall and a wall constructed of prefab panels to which modular patient service equipment has been coupled;

FIGS. 6–8 are perspective views of a two walls of a patient room with a conventional wall plumbed and wired with outlets and couplings to which various modular patient service equipment is attached to form a headwall;

FIGS. 9 is a perspective view of a wall formed from an alternative embodiment of wall panels providing concealable lighting, gas and electrical services;

FIG. 10 is a cross-sectional view of the alternative wall panel of FIG. 9 showing the lighting and electrical and gas connections positioned to provide patient services;

FIG. 12 is a perspective view of a patient room created from alternative wall panels including pre-wired and pre-plumbed patient services which are concealed;

FIG. 13 is a perspective view of two alternative wall panels including pre-wired and pre-plumbed patient services which can be concealed showing the panel on the right having lighting and electrical and gas services in their non-concealed positions and the panel on the left having the lighting and electrical and gas services concealed;

FIG. 14 is a perspective view of a patient room with one wall removed for clarity including a headwall and an entry wall formed from wall panels, a bathroom formed from a sink panel, a wall panel, an entry panel, and a shower unit with modular patient service equipment attached to the headwall;

DETAILED DESCRIPTION OF THE DRAWINGS

Figure 1:
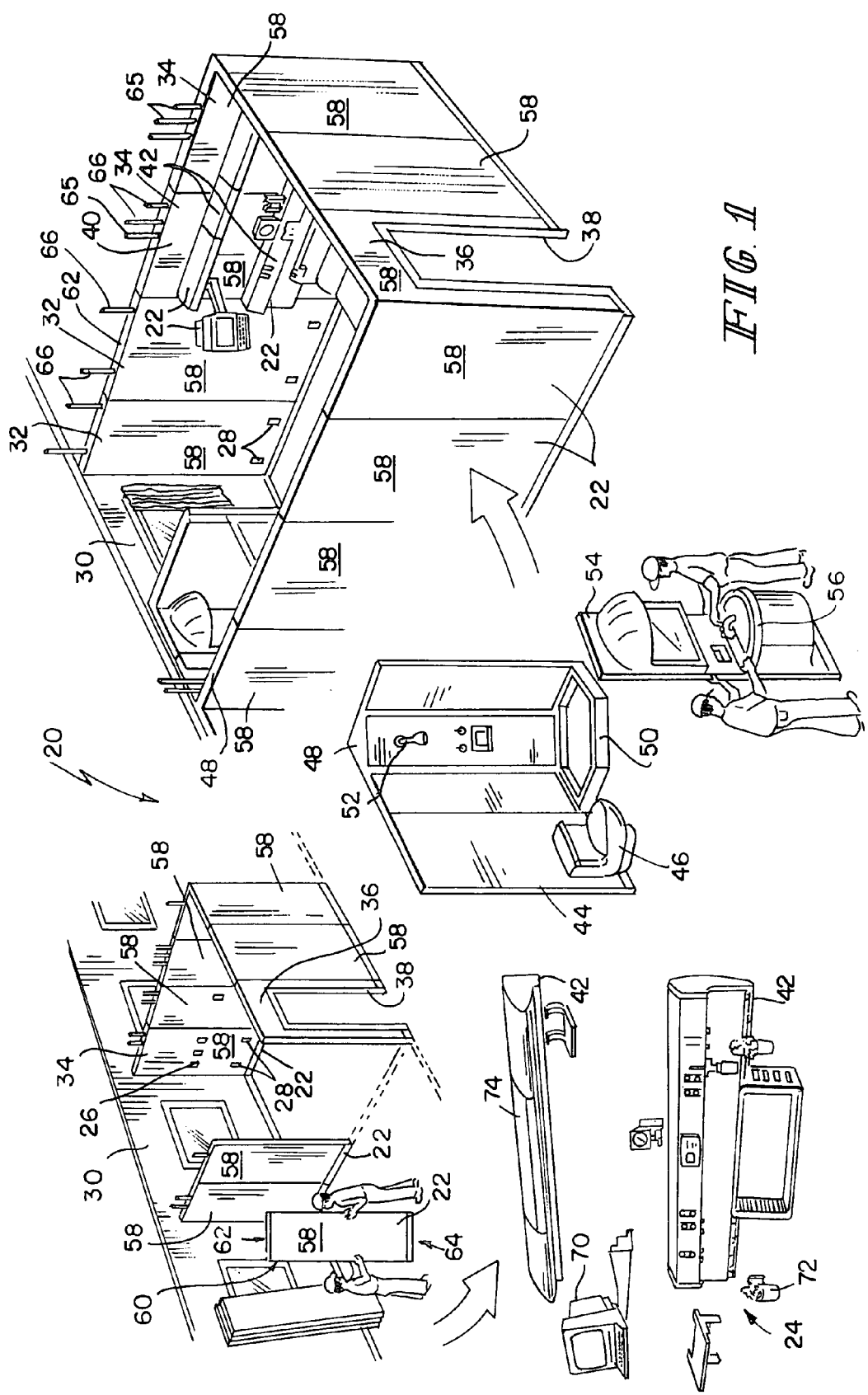
FIG. 1 illustrates the assembly of a patient room from variously configured wall panels and modular patient service equipment.
Figure 5:
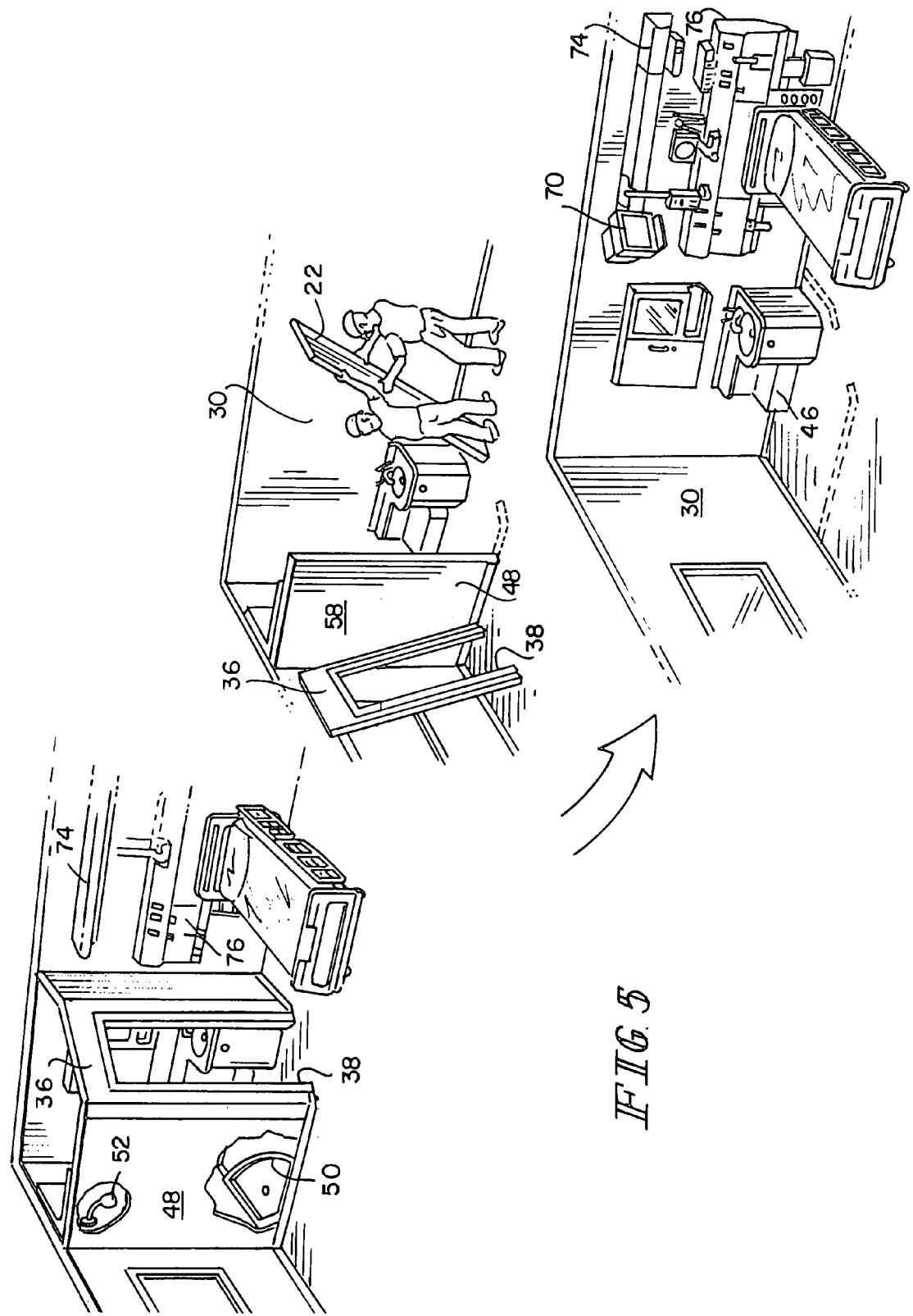
FIG. 5 includes three time lapse perspective views of a patient room which originally included a modular shower unit, a passageway wall panel and another wall panel forming an enclosed bathroom which is disassembled to provide an open bathroom more conducive to intensive care.
Figure 11:
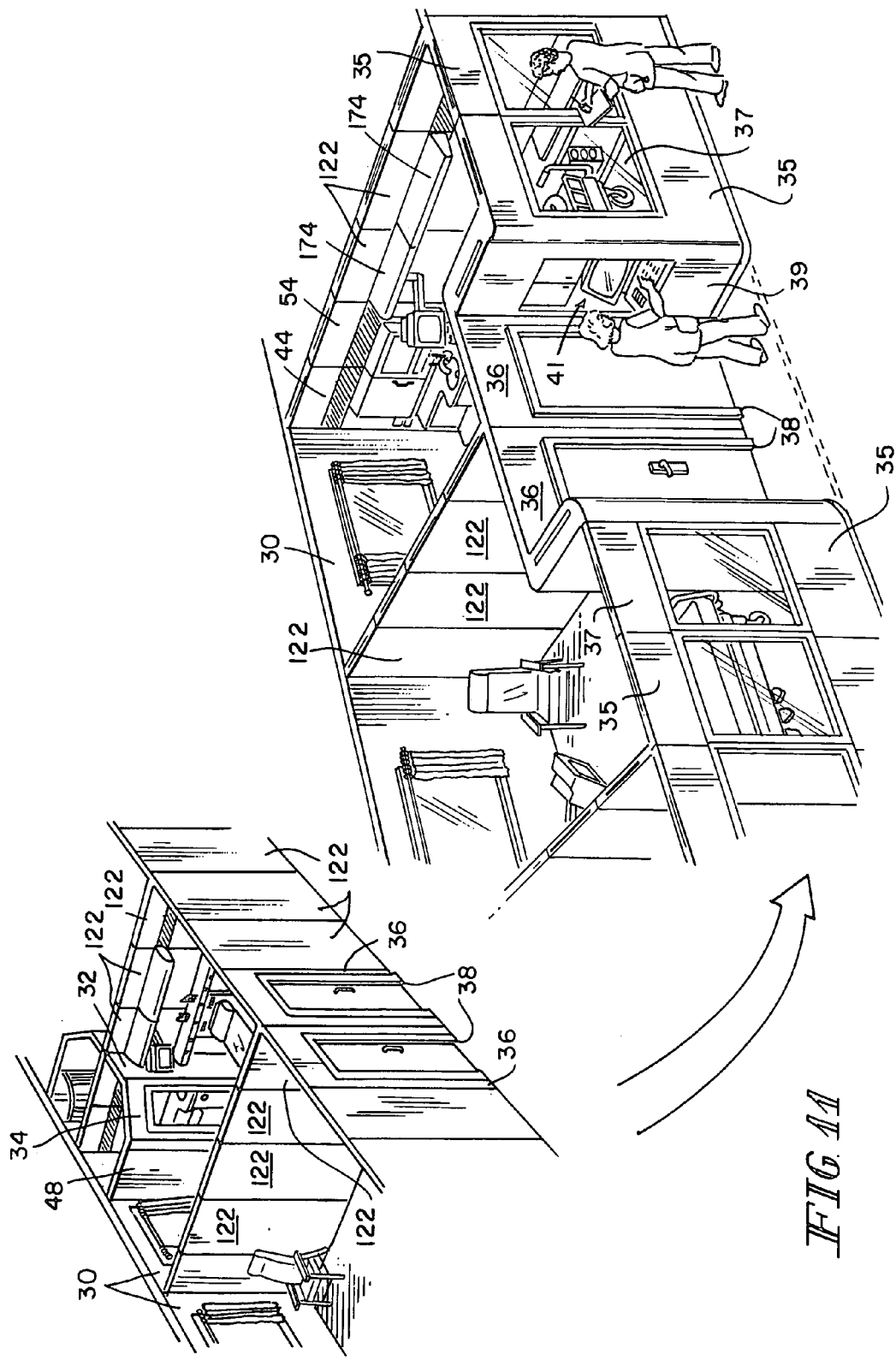
FIG. 11 includes two time lapse perspective views of two adjacent patient rooms formed from alternative wall panels and modular patient service equipment being converted from a medical surgical complex to a critical care unit.

As shown in FIG. 1, an adaptable clinical environment or modular patient room 20 includes variously configured wall panels 22 and modular patient service equipment 24. Modular patient service equipment 24 may be connected to couplings 26 and outlets 28 formed in wall panels 22 or conventional walls 30. Prefabricated modular wall panels 22 are designed to be joined together and to existing conventional walls 30 to facilitate the creation of and reconfiguration of patient rooms. Modular wall panels 22 are configured for rapid clean installation and for joining to permanent conventional walls 30 or other modular wall panels 22 in multiple configurations so that a healthcare facility floor space can be customized to suit patient needs.

Various configurations of modular wall panels 22 are provided, including an electrical outlet panel 32 including one or more electrical outlets 28 hardwired therein, an electrical/gas panel 34 including one or more electrical outlets 28 hardwired therein and one or more gas outlets 26 plumbed therein, a entry way panel 36 formed to include a door frame 38 therein, a window panel 35 formed to include a window 37 therein, a headwall panel 40 including hardwired and brazed electrical and gas connections 28, 26 configured for receipt of modular headwall components 42 of modular patient service equipment 24. An alcove wall panel 39 formed to include a computer station 41 is also designed for modular assembly. A modular bathroom is also provided which includes a toilet panel 44 with a toilet 46 attached thereto and properly plumbed with water supply lines and waste water disposal lines (not shown), a shower unit 48 with basin 50 and shower head 52 appropriately plumbed for water supply and waste water disposal (not shown), a sink panel 54 with a sink basin 56 attached thereto and appropriately plumbed for water supply and disposal (not shown). The supply and disposal lines are not shown as they extend through the interior of the unit.

It is within the scope of this disclosure for shower unit 48 and toilet panel 44 to be integrated together such that toilet 46 is situated above or on basin 50. In such a water-using device having toilet 46 situated above or on basin 50, a patient may sit on toilet 46 (or an associated toilet seat cover), if desired, during showering. Such a water-using device is well suited for patients who are not able to stand for long periods of time or who are unable to stand at all. In some embodiments, a bed pan washer is integrated into toilet 46.

It will be understood that all wall panels 22 include oppositely facing spaced apart wall surfaces 58 with side walls 60 extending therebetween, a top surface 62, and a floor engaging surface 64 defining an interior of the panel 22. Wall panels 32, 34, 40, 39, 44, 54 and units 48 with electrical outlets 28 and or gas couplings 26 extending through the wall surface 58, and/or plumbing connections (not shown) have the conduits 65 including wiring 66 and piping 68 arranged to extend through the interior of the panel 22 or unit between the outlet 28, coupling 26, and/or connection and the top surface 62 through which the wiring or plumbing extends. Healthcare facilities typically include false ceilings above which electrical, gas, and plumbing supply lines extend. Wiring 66 and piping 68 extending through top surface 62 for connection to supply lines above the false ceiling.

Modular patient service equipment 24 includes modular headwall components 42 and other components such as, a monitor 70, a pressure regulator 72 and the like. Multiple headwall components 42 are also provided including a lighting unit 74, a Hi-Acute headwall unit 76, a lo acute headwall unit 78, and a mobile headwall unit 80 all of which are available from Hill-Rom, Inc, Batesville, Ind. It will be understood that, the outlets 28 and couplings 26 extending through wall surface 58 of wall panels 22 are arranged and configured to mate with coupling and connectors on the modular patient service equipment 24 so that power, fluids, pressurized gasses, and vacuum may be supplied to the modular patient service equipment 24 upon connection of the same to a wall panel 22.

An alternative wall panel 122 is illustrated in FIGS. 9–14. Wall panels 122 include oppositely facing spaced apart wall surfaces 158 with side walls 160 extending therebetween, a top surface 162, and a floor engaging surface 164 defining an interior of the panel 122. Illustratively, wall panel 122 is formed to include a laterally extending light cavity 182 extending inwardly from wall surface 158 and includes a lighting unit 174 pivotally mounted within cavity 182. Illustratively, lighting unit 174 includes a panel 184 having a decorative surface 186 and a light housing surface 188. Light panel 184 is pivotally mounted at one end 190 to top 192 of cavity 182 so that when light panel 184 is pivoted inwardly decorative surface 186 lies substantially parallel to wall surface 158 while light housing surface 188 is disposed within cavity 182 and concealed from view. As shown in FIG. 10, when panel 184 is rotated 90 degrees, light housing surface 188 is disposed so that an electric light 194, such as an incandescent or florescent bulb, can provide illumination to the room. Power is provided to light 194 through internal wiring 166 in wall panel 122.

Wall panel 122 also includes a laterally extending service cavity 196 within which electrical outlets 128 and gas couplings 126 are positioned. A service panel 198 having a decorative side 197 and a fixture-facing side 195 is pivotally mounted at one end 193 to top 191 of service cavity 196. When service panel 198 is rotated inwardly, decorative side 197 is substantially parallel to wall surface 158 and electrical outlets 128 and gas couplings 126 are concealed. When service panel 198 is rotated outwardly, access is provided to electrical outlets 128 and gas couplings 126 for connection of modular patient service equipment 24 thereto.

As shown, for example, in FIG. 13, couplings 127 and connectors 129 are provided in side walls 160 to connect internal electrical wiring 166 and gas piping 168 of adjacent wall panels 122 when they are connected. The wiring 166 and piping 168 extends through the interior of the panel 122 to provide electricity to outlet 128, and gas to coupling 126. Wiring 166 and plumbing 168 also extend through top surface 162 to connect to gas and electric supply lines in the ceiling.

Figure 15:
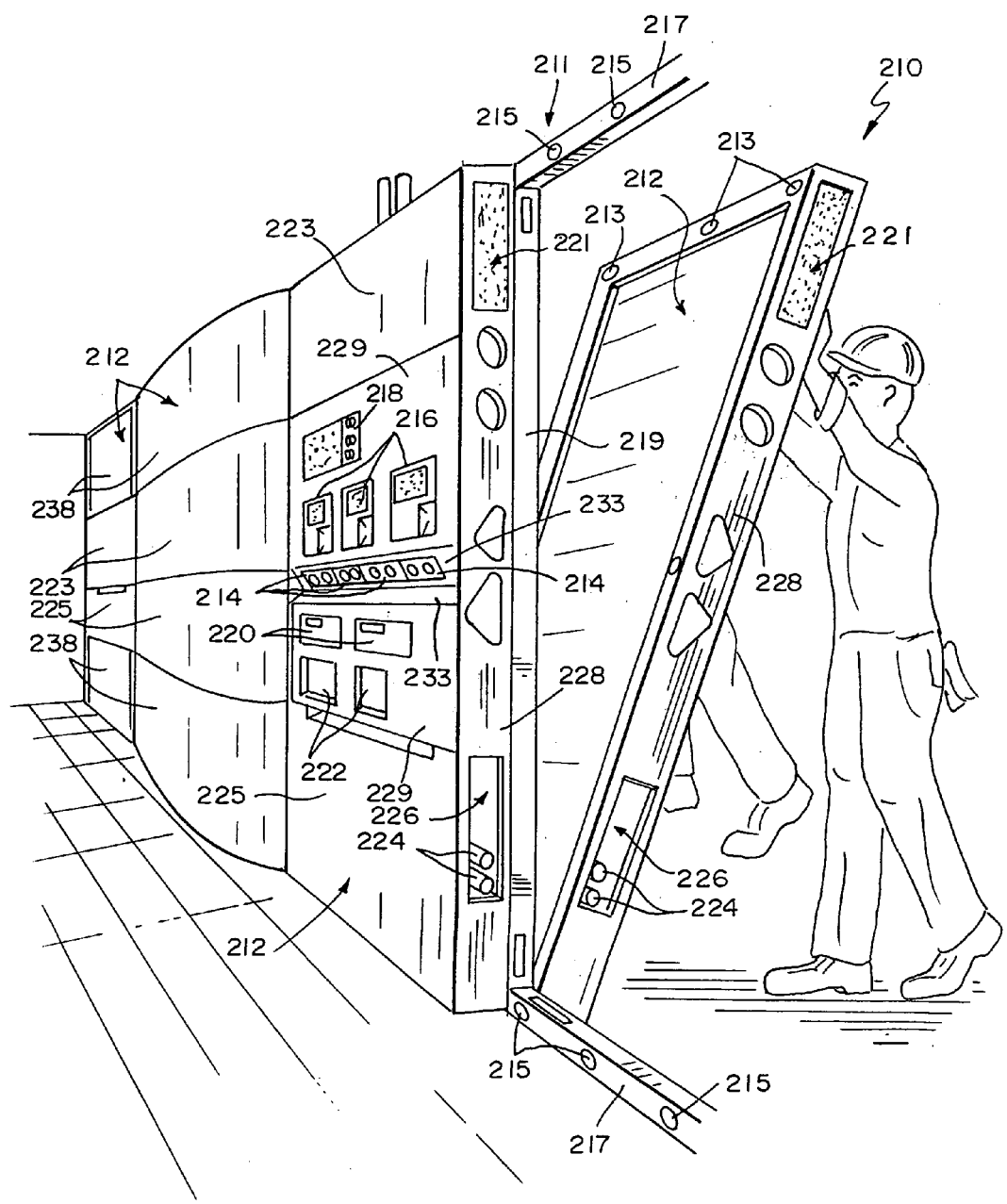
FIG. 15 is a perspective view of a pair of modular wall units being installed in a hospital showing a first modular wall unit extending between a floor and a ceiling of the hospital, a second modular wall unit being pivoted into place in a back-to-back arrangement with the first modular wall unit, the first modular wall unit including a plurality of service-delivery outlets located about midway between a top end and a bottom end of the first modular wall unit, three gas-flow meters included in the first modular wall unit positioned above the plurality of service-delivery outlets, a data monitor included in the first modular wall unit positioned above the gas-flow meters, and environmental control panels included in the first modular wall unit positioned below the service-delivery outlets.

According to this disclosure, a modular wall system 210 includes a plurality of modular wall units 212 extending between a floor and a ceiling of a hospital as shown in FIG. 15. A skeletal framework 211 is fixed to the floor and to the ceiling of the hospital. Illustrative framework 211 has horizontal frame members 217 and vertical frame members 219. Frame members 217 are mounted either to the floor or to the ceiling and frame members 219 extend between frame members 217. In some embodiments, frame members 217, 219 are tubular members having hollow interior regions; in other embodiments, frame members 217, 219 are channel members that are open on one or more sides; and in still other embodiments, frame members 217, 219 are solid members.

In some alternative arrangements, frame members 217 are omitted such that wall units couple only to frame members 219, and in other alternative arrangements, frame members 219 are omitted such that wall units couple only to frame members 217. Other structures to which units 212 couple in lieu of framework 211 are contemplated by this disclosure. For example, in some embodiments, wall units 212 are configured to couple to tabs, flanges, brackets, posts, or the like that extend from the floor or from the ceiling or from both, and in other embodiments, wall units 212 are fastened directly to the floor or to the ceiling or one or more walls or to combinations of these.

Wall units 212 are particularly suited for use in hospitals to construct patient rooms or for use in other healthcare facilities, including nursing homes, outpatient clinics, and the like, to construct rooms of various types. In some embodiments, wall units 212 couple to framework 211 in a back-to-back arrangement. Such an arrangement is used, for example, when wall system 210 divides one hospital room from another hospital room. In other embodiments, one side of framework 211 abuts, or is situated alongside, an existing hospital wall and one or more wall units 212 couple to the other side of framework 211.

Each illustrative wall unit 212 includes couplers 213 that engage mating couplers 215 included in or mounted to framework 211. Couplers 213, 215 may include, for example, hooks, posts, latches, clasps, clamps, snaps, slots, fingers, flanges, pins, and the like, as well as combinations of these. For example, in some embodiments, one set of couplers 213, 215 comprises headed pins and the other set of couplers 213, 215 comprises keyhole-shaped slots that receive the headed pins in a manner well known to those skilled in the art. In some embodiments, couplers 215 of framework 211 comprise pins that extend through holes formed in wall units 212 into the interior region of units 212 to be engaged by movable hooks, latches, clasps, or other suitable grippers. In such embodiments, a release mechanism, such a lever, handle, knob, button, or the like, is coupled to each of the associated grippers and is accessible through an access port 221 of the respective unit 212 for actuation to release the associated grippers, of whatever type, from the associated pins to permit decoupling of the associated wall unit 212 from framework 211.

Modular wall units 212 are prefabricated in a variety of styles having one or more of the following types of built-in, service-delivery equipment: electrical services (such as electrical power and data lines), gas services (such as gas delivery and suction lines), conduits (such as water delivery or drain lines, as well as conduits for wire pass through), raceways (such as vertical or horizontal mounting tracks), monitors (such as monitor 70 mentioned above), communication devices (such as telephone or intercom equipment), gas blocks, manifolds, gas-flow meters, supply shelves, display screens, windows (such as window 37 described above), sinks (such as sink 56 described above), hand-washing monitors (such as described in U.S. patent application Ser. No. 09/699,796 for HYGIENE MONITORING SYSTEM which was filed Oct., 30, 2000 and which is hereby incorporated by reference herein), drawers, water-supply devices, baths, and flip-down work surfaces. For example, an illustrative modular wall unit 212, shown in FIG. 15, includes a plurality of gas and/or electrical service-delivery outlets 214, a plurality of gas-flow meters 216, a data monitor 218, a pair of environmental control panels 220, and a pair of water-supply modules 222. Water-supply modules 222 are referred to elsewhere in this disclosure as water dispensers.

Electrical services accessible via appropriately configured outlets 214 include, for example, electrical power or data transfer lines. Data transfer lines comprise lines coupled to a computer network, audio lines, video lines, telephone lines, and the like. Gas services accessible via appropriately configured outlets 214 include, for example, delivery of any type of gas such as oxygen, nitrogen, carbon dioxide, nitrous oxide, hydrogen, argon, etc. and delivery of suction, including suction used for waste anesthesia gas disposal. Meters 216 include indicators that provide a visual display of the pressure of the gas services delivered to associated outlets 214.

Data displayed on monitor 218 includes, for example, data pertaining to patient physiological conditions (such as heart rate, respiration rate, blood pressure, blood oxygenation levels, and the like), other patient data (such as name, medical condition, laboratory results, the patient's doctor, etc.), data pertaining to gas or electrical services delivered via outlets 214, environmental data (such as room temperature, humidity, barometric pressure, etc.), supply management data (such as the patient's prescribed medications, dosage levels for medications, a list of equipment used to provide care to the patient, and lists of miscellaneous items to be stocked in the patient's room, etc.). If monitor 218 is coupled to a computer that is, in turn, coupled to the computer network of the healthcare facility, then any data available on the computer network (including data available on the world wide web, aka the Internet) may be displayed on monitor 218.

Environmental control panels 220 include user inputs that are used to adjust, for example, room temperature or room lighting. In some embodiments, panels 220 include user inputs for controlling entertainment equipment, such as a radio or television. Water-supply modules 222 are configured to supply filtered and/or sterilized water to the point of care for the patient. Details of water-supply modules (aka water dispensers) are provided below with reference to FIGS. 17–20.

Figure 16:
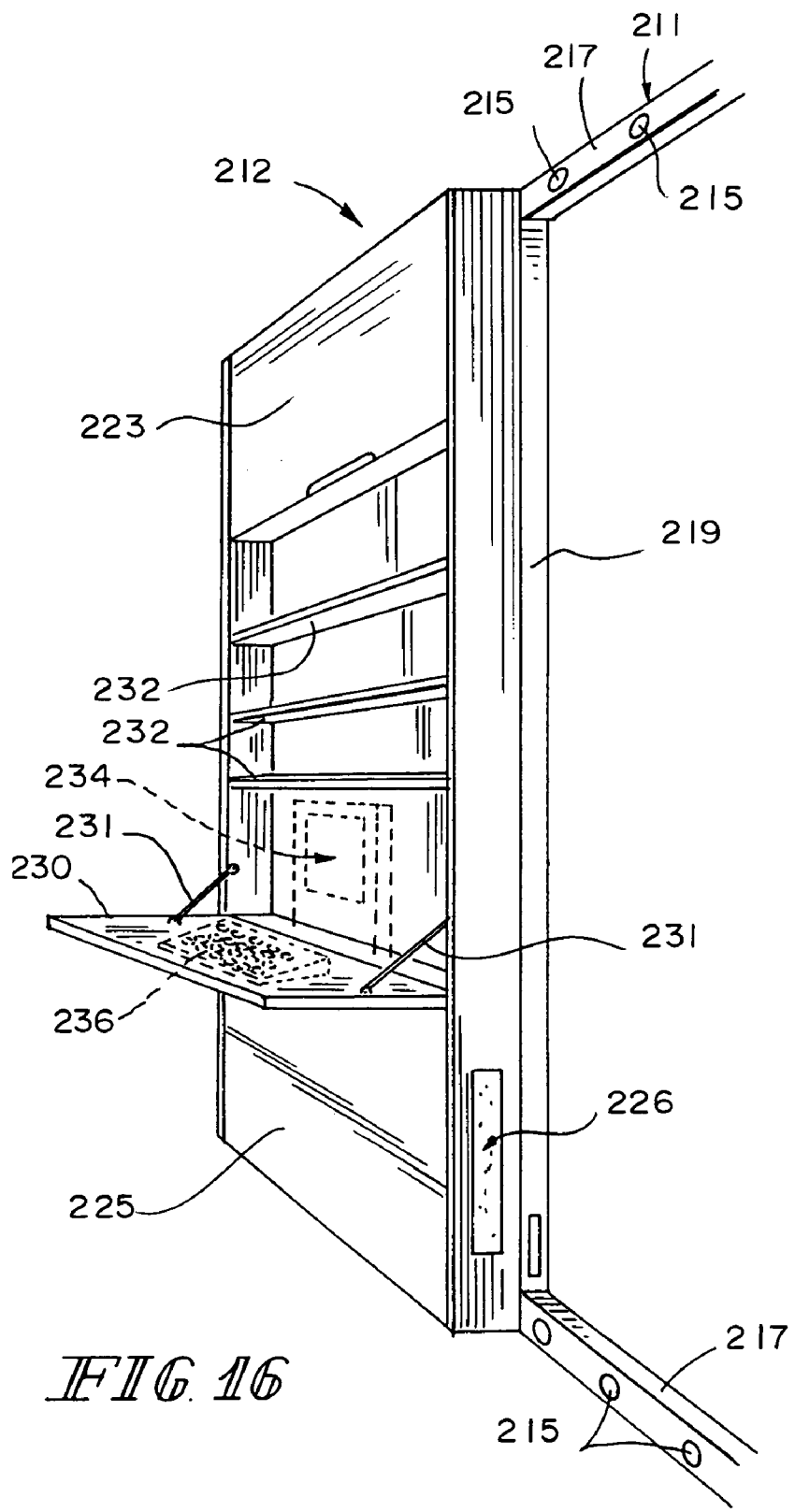
FIG. 16 is a perspective view similar to FIG. 15 showing an alternative modular wall unit having a flip-down work surface, a keyboard (in phantom) supported on the work surface, a computer monitor (in phantom) situated in a recess adjacent the work surface, and a set of supply shelves above the computer monitor.

Wall units 212 of FIGS. 15 and 16 each have a vertically movable upper door panel 223 and a vertically movable lower door panel 225. Panel 223 of wall unit 212 of FIG. 15 is movable between a lowered position covering meters 216 and monitor 218 and a raised position exposing meters 216 and monitor 218 for use. Panel 225 of wall unit 212 of FIG. 15 is movable between a raised position covering outlets 214, panels 220, and modules 222 and a lowered position exposing outlets 214, panels 220, and modules 222 for use. Wall unit 212 has stationary upper and lower front panels 229 that extend substantially vertically. Wall unit 212 also has a pair of stationary inclined panels 233 situated between panels 229.

Meters 216 and monitor 218 are embedded in wall unit 212 such that front faces or portions of these devices project beyond the upper front panel 229 by only a minimal amount, if at all. Similarly, control panels 220 and modules 222 are embedded in wall unit 212 such that front faces or portions of these devices project beyond the lower front panel 229 by only a minimal amount, if at all. Outlets 214 are mounted on inclined panels 233 so as not to project beyond a plane defined by the front surfaces of the upper and lower front panels 229.

Wall units 212 each have a pair of spaced apart side walls 228. The vertical edges of movable panels 223, 225 or, alternatively, members attached to panels 223, 225 adjacent the side edges, are received in tracks that are formed in or that are coupled to side walls 228 or panels 229. In some embodiments, vertical edges of panels 223, 225 slide in the tracks of side walls 228 or panels 229 and in other embodiments, rollers or friction-reducing pads are provided to guide the movement of panels 223, 225 relative to side walls 228 or panels 229, as the case may be.

In some embodiments, panels 223, 225 are movable independently of one another between the respective raised and lowered positions. In other embodiments, panels 223, 225 are interconnected by a suitable linkage mechanism, such as a set of cables and pulleys or a set of chains and sprockets, so that upward movement of panel 223 results in downward movement of panel 225 and vice versa. Wall units 212 have suitable locking mechanisms, such as latches, pins, clutches, hooks, or the like, that lock doors 223, 225 in the respective raised and lowered positions and that are released, via a release handle, lever, knob, switch, or the like, to unlock doors 223, 225. Panels 223, 225 are substantially planar in some embodiments, as shown in the "outer" wall units 212 of FIG. 15, and panels 223, 225 are curved in other embodiments, as shown in the "center" wall unit 212 of FIG. 15. Wall units 212 with curved panels 223, 225 have larger interior regions and therefore, are able to have more or larger pieces of equipment prefabricated therein or mounted thereto.

Data lines, gas lines, vacuum lines, power lines, and water lines are coupled to associated equipment, such as, outlets 214, meters 216, monitor 218, panels 220, and modules 222. Appropriately configured connectors 224, shown in FIG. 15, are coupled to ends of these various lines and are accessible either through openings 226 formed in side walls 228 of wall units 212 or through openings (not shown) formed in a top wall (not shown) of wall units 212. The top walls of units 212 are similar to the top walls of wall panels 22, 122 shown in FIGS. 1–14.

Connectors 224 that are accessible through openings 226 associated with a particular wall unit 212 mate with corresponding connectors of the next adjacent wall unit 212. Thus, wall units 212 each include line segments that deliver services to associated equipment such as, outlets 214, meters 216, monitor 218, panels 220, and modules 222 included in wall units 212 or that deliver services to the line segments of the next adjacent wall unit 212. Connectors 224 that are accessible through openings formed in the top wall of wall units 712 couple to other hospital service lines (not shown) to receive services therefrom. In some instances, connectors 224 are gas connectors (or suction connectors); in other instances, connectors 224 are electrical connectors; and in still other instances, connectors 224 are water connectors.

With regard to some embodiments having connectors 224 accessible through openings 226, connectors 224 of one wall unit 212 mate with connectors 224 of the next adjacent wall unit 212 automatically. If one set of couplers 213, 215 comprises headed pins and if the other of connectors 215 comprises keyhole-shaped slots, as described above, then the automatic mating occurs, for example, as a result of one of wall units 212 being moved horizontally toward a stationary, next-adjacent wall unit 212 after the wall unit 212 to be moved has been placed in an upright position against framework 211. In such embodiments, a portion of one set of connectors 224 enters into the interior region of the next adjacent wall unit 212 to mate with the associated second set of connectors 224 which are aligned with the first set of connectors 224. In other embodiments, front access panels 238 of wall units 212 are removable to permit access to the interior regions of wall units 212 so that connectors 224 can be manipulated by personnel or so that separate connector pieces (not shown) can be mated with connectors 224 of the side-by-side wall units 212.

Another illustrative wall unit 212, shown in FIG. 16, includes a flip-down work surface 230 and a set of supply shelves 232. A pair of braces 231, such as cables, ropes, chains, or articulated linkages, supports work surface 230 in a horizontal use position as shown in FIG. 16. Work surface 230 is pivotable from the use position to a vertical storage position. Wall unit 212 has a suitable locking mechanism to lock work surface 230 in the storage position. Optionally, a computer monitor 234 may be integrated into the wall unit 212 and a keyboard 236 may be attached to or placed on work surface 230 as shown in FIG. 16 (in phantom). Electrical lines are routed to monitor 234 or to any other equipment integrated into wall unit 212 through, for example, opening 226 of side wall 228 of the wall unit 212 of FIG. 16.

Wall units 212 may be configured, as desired, to include any of the features or devices that are included in or couplable to any of the panels 22, 32, 34, 36, 35, 40, 39, 44, 54, 122 described above with reference to FIGS. 1–14. Furthermore, wall units 212 having visitor seating, a flip-down guest bed, a writing desk, a closet or other room furniture built therein are within the scope of this disclosure. Flip-down guest beds and visitor seats are similar to flip-down work surface 230, except that the beds and seats are appropriately sized for the intended use (lying down or sitting) and have cushions or pads coupled thereto. In some embodiments, the beds and seats of units 212 have legs that engage the floor of the hospital room to provide additional support to the associated beds and seats when moved to the respective use positions.

Based on the preceding discussion, it will be appreciated that wall units 212 can be set up or taken down with simple tools and without creating much, if any, dust, debris or excessive noise. In those embodiments of wall units 212, having one or more windows 37, some or all of the windows 37 may be a liquid crystal display (LCD) window that is normally transparent, but that becomes opaque when a voltage is applied thereto. In such embodiments of wall units 212 having one or more LCD windows, an appropriate number of switches are provided on the wall unit 212 for changing the associated LCD windows from the transparent configuration to the opaque configuration. It is within the scope of this disclosure for any of the above-mentioned equipment included in wall units 212 to be coupled electrically to a computer network of the hospital to communicate information about the equipment to the network. The information communicated to the network from wall units 212, therefore, may be viewed on a remote computer terminal, such as a computer terminal at a nurse station.

Figure 17:
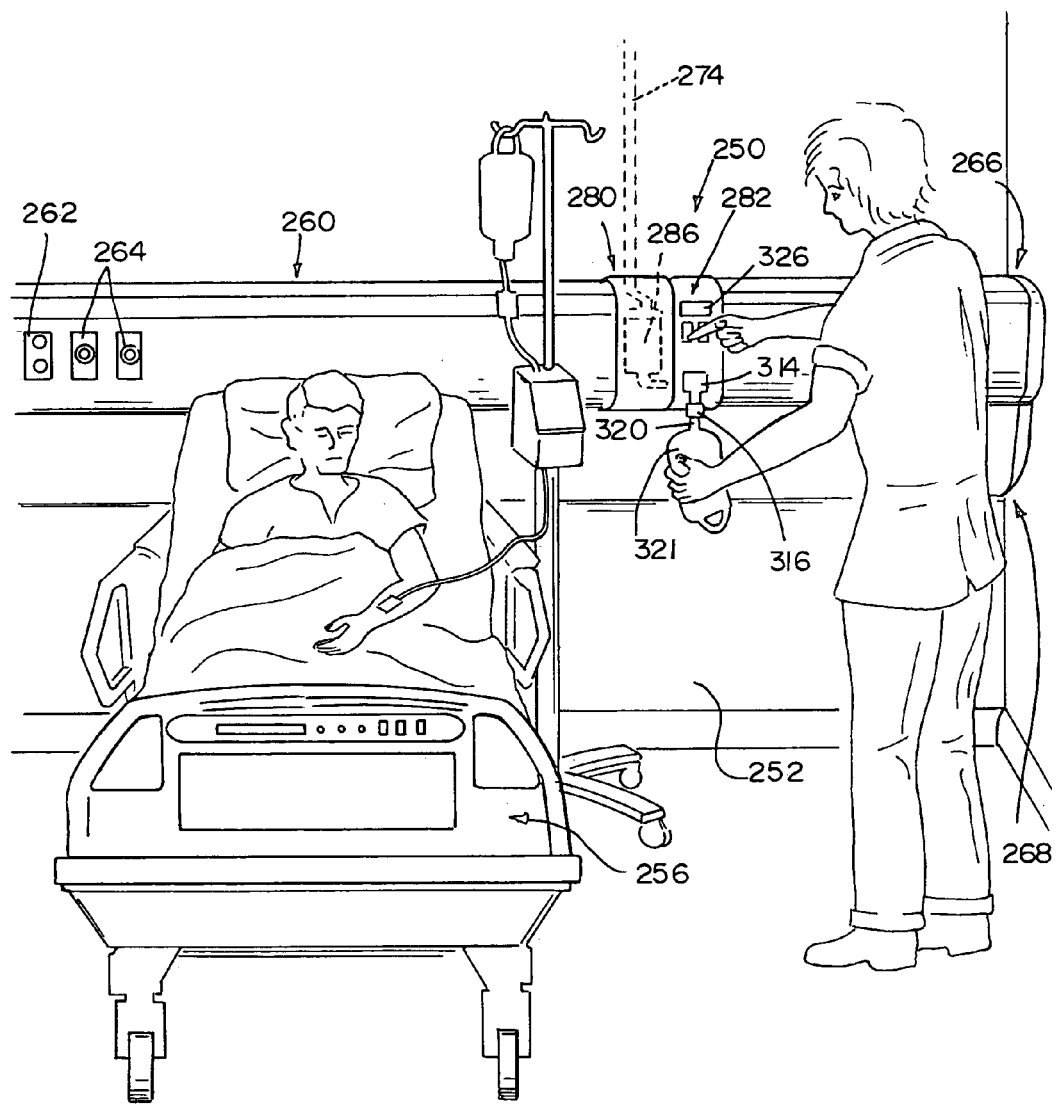
FIG. 17 is a perspective view of a portion of a patient room showing a patient resting in a hospital bed, a caregiver standing at a point of care in the hospital room, the caregiver filling an IV bag with water dispensed by a water dispenser that is coupled to a headwall unit mounted to a wall of the patient room.
Figure 18:
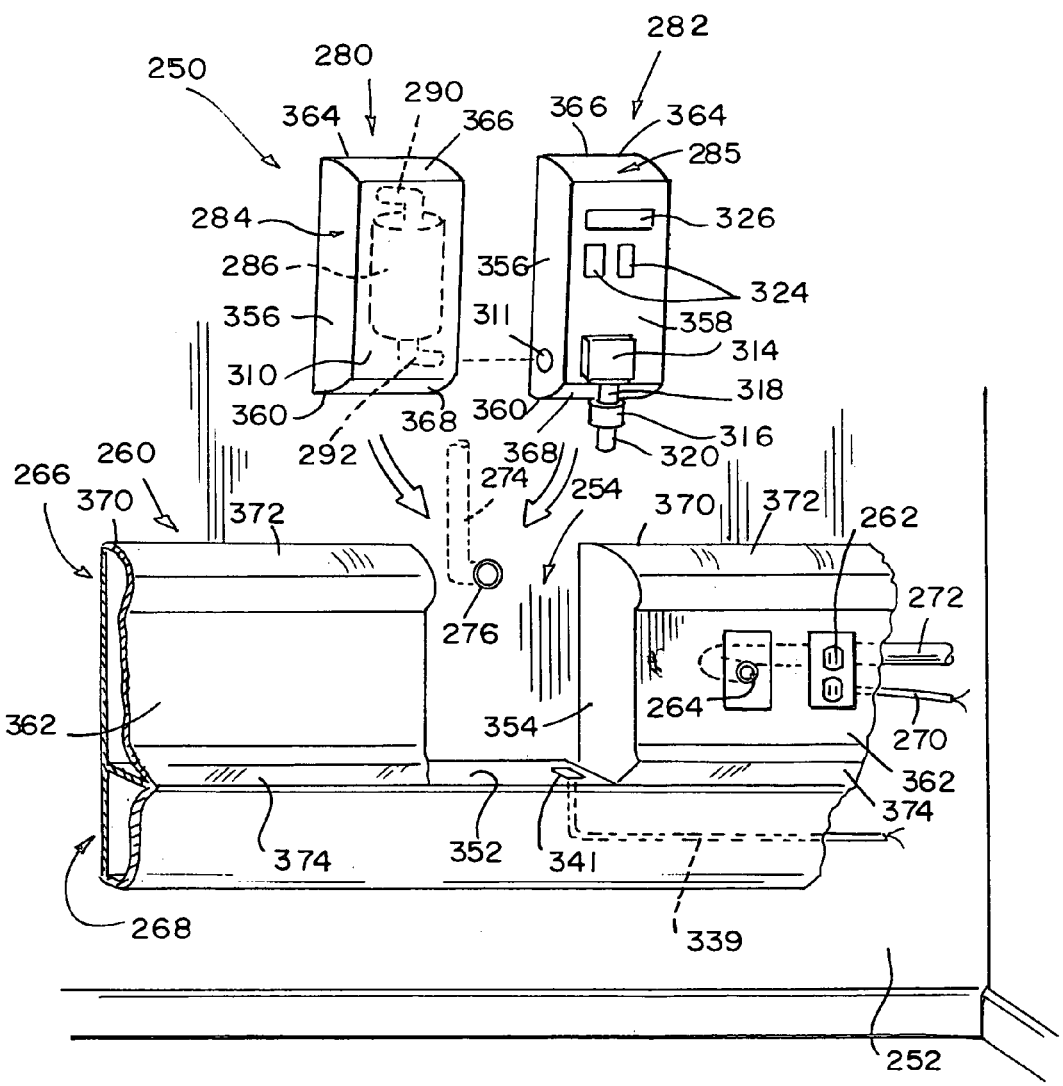
FIG. 18 is an exploded perspective view of a portion of the patient room of FIG. 17 showing the headwall unit having a cavity, the water dispenser having a filter module and a dispenser module, and the cavity being sized to receive the filter and dispenser modules.

Referring now to FIGS. 17 and 18, a water dispenser 250 is coupled to a headwall unit 260 that is mounted to a wall 252 of a patient room. Illustrative headwall unit 260 has a cavity 254, shown best in FIG. 18, that is configured to receive dispenser 250 as shown in FIG. 17. It is within the scope of this disclosure for headwall unit 260 to have a variety of configurations and features, such as, for example, those shown and described in U.S. Pat. Nos. 6,145,253; 5,890,326; 5,756,933; 5,653,064; 5,323,565; 5,060,425; 4,821,470; and 4,338,485; each of which is hereby incorporated by reference herein.

A hospital bed 256 that supports a patient is arranged so that a head end of hospital bed 256 is adjacent headwall unit 260 as shown in FIG. 17. In other arrangements, the head end of bed 256 is adjacent a bed locator which is either coupled to or separate from headwall unit 260. Thus, a bed locator, itself, is considered to be a "headwall unit" within the scope of this disclosure, as are units like unit 260 without bed locators and units with bed locators integrated therewith or coupled thereto.

The areas or zones around hospital bed 256 within the hospital room are considered to be "points of care" for the patient. That is, caregivers attend to the needs of patients when in the points of care. Although headwall unit 260 and water dispenser 250 is discussed herein in the context of a patient room in a hospital, it is within the scope of this disclosure for headwall unit 260 and water dispenser 250 to be used in other environments such as a nursing home, outpatient surgery facility, and the like.

Headwall unit 260 is in the point of care for the patient and includes electrical outlets 262 and gas outlets 264. Illustrative headwall unit 260 has a horizontal upper chase 266 and a horizontal lower chase 268 beneath upper chase 266. In the illustrative embodiment, one or more electrical lines 270 and gas lines 272 are routed to associated outlets 262, 264, respectively, through upper chase 266. In alternative embodiments, lower chase 268 has outlets 262, 264 coupled thereto and associated lines 270, 272 are routed through lower chase 268.

In the illustrative embodiment, a water line 274 of the healthcare facility is situated behind wall 252 and is accessible in cavity 254 through an opening 276 formed in wall 252 as shown in FIG. 18. In alternative embodiments, water line 274 is routed through either upper chase 266 or lower chase 268 or portions of both. Water line 274 couples to dispenser 250 to supply water to dispenser 250. The dispenser 250 is operable to dispense water from water line 274 to the point of care.

Water dispenser 250 includes a first module 280 and a second module 282 as shown in FIGS. 17–20. In alternative embodiments, modules 280, 282 are formed as a single, integral module. First module 280 receives water from line 274 and either filters the water, sterilizes the water, or both. Second module 282 receives the filtered and/or sterilized water from module 280. In the embodiment of module 280 shown in FIGS. 17–19, module 280 has a housing 284 and a filter 286 situated in an interior region of housing 284. In the embodiment of module 280 shown diagrammatically in FIG. 20, module 280 has a sterilizer 288 situated in the interior region of housing 284. Sterilizer 288 operates to sterilize water. In some embodiments, one of the components of sterilizer 288 is a filter. Module 282 has various components, described below, that control the dispensing of water to the point of care. Module 282 has a housing 285 in which various other components of module 282, such as electrical circuitry, are situated.

Filter 286 comprises, for example, a carbon filter, a fiber filter, a reverse osmosis filter, or the like. Carbon filters typically comprise cartridges having porous surfaces and are packed with charcoal. Fiber filters typically have cellulose or rayon fibers that are tightly wrapped. Reverse osmosis filters force water through a semi-permeable, nonporous synthetic membrane, such as a cellulose acetate membrane. Thus, the term "filter" as used in this disclosure, including in the claims, is intended to cover devices of all types that are capable of filtering water. Such filters are available commercially from companies such as Culligan International Company of Northbrook, Ill. and Brita Products Company of Oakland, Calif.

There are many devices and methods known for sterilizing water and this disclosure contemplates that sterilizer 288 may be appropriately configured to sterilize water via any of these devices or methods or combination thereof. For example, exposure of water to ultraviolet light is one method of water sterilization. See U.S. Pat. Nos. 6,235,191; 6,193,894; 5,622,622; 4,755,292; and 4,535,247. Sterilization of water via a heat exchanger (i.e. boiling/ condensing the water or heating/cooling the water) is another method of water sterilization. See U.S. Pat. Nos. 6,212,333; 6,059,965; 5,498,396; and 5,487,814. Electrolysis is yet another method of water sterilization. See U.S. Pat. Nos. 5,897,757; 5,439,576; 5,395,492; 4,946,574; 4,761,208; and 4,451,341. Chemically treating water to sterilize the water is a further method of water sterilization. See U.S. Pat. No. 4,594,154 (soda hypochlorite or chlorine gas); U.S. Pat. No. 4,043,932 (sodium-silver-chloride complex); and U.S. Pat. No. 3,975,271 (mixture of chlorine and a salt of another halogen, such as bromine and/or iodine). Filtering the water, possibly in stages and possibly in combination with other water treatment, is still another method of sterilizing water. See U.S. Pat. No. 5,851,388(iodine resin filter); U.S. Pat. No. 5,573,666 (filter/ultraviolet light); U.S. Pat. No. 5,556,279 (activated charcoal filter/iodinated fixed rate exchange resin filter); U.S. Pat. No. 5,384,032 (resin filter/charcoal filter/ ultraviolet light); U.S. Pat. No. 5,068,030 (carbon filter/ microwave oscillator/ultraviolet light); U.S. Pat. No. 4,615,799 (activated carbon filter/ultraviolet radiation) and U.S. Pat. No. 4,342,651 (reverse osmosis filter). Other miscellaneous water sterilization devices and methods can be found in U.S. Pat. No. 6,071,473 (ultrasonic vibrations/ultraviolet light); U.S. Pat. No. 5,447,640 (ozonized water); U.S. Pat. No. 5,273,713 (dyeing/irradiation); U.S. Pat. No. 5,158,454

(ozone radical converter); and U.S. Pat. No. 4,857,204 (ultraviolet light/magnetic field). All of the patents mentioned in this paragraph are hereby incorporated by reference herein to provide general information about water sterilization. Thus, the term "sterilizer" as used in this disclosure, including in the claims, is intended to cover devices and methods of all types that pertain to sterilizing water.

Figure 19:
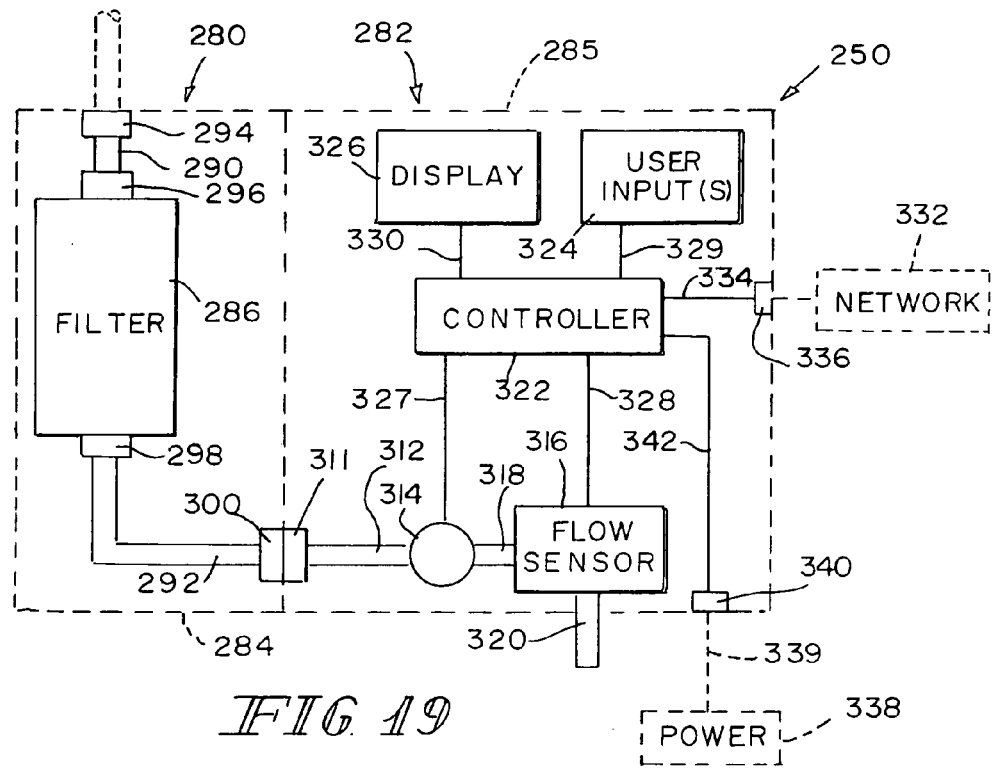
FIG. 19 is a diagrammatic view of the water dispenser of FIG. 18 showing the dispenser module having an electric circuit including a controller, one or more user inputs, a display, and a flow sensor, the controller being coupled electrically to a control valve, the controller being couplable to a network and to a supply of power, and showing the filter module having a filter that is couplable to an external water line and to a water line of the dispenser module that leads to the control valve.

Module 280 of FIGS. 17–19 has an inlet line 290, an outlet line 292, a first coupler 294 that couples inlet line 290 to line 274 of the healthcare facility, a second coupler 296 that couples inlet line 290 to an inlet port of filter 286, a third coupler 298 that couples outlet line 292 to an outlet port of filter 286, and a fourth coupler 300 that couples outlet line 292 to module 282. Filter 286 is replaceable and therefore, couplers 296, 298 are manipulatable to attach and detach filter 286 from lines 290, 292. To gain access to filter 286, a front panel or wall 310 of housing 284 is either pivotable relative to the remainder of housing 284 to an opened position or is completely removable from the remainder of housing 284. A lock (not shown) locks panel 310 in a closed position so that only personnel with appropriate keys, tokens, or access codes have access to filter 286 for inspection, repair or replacement.

Figure 20:
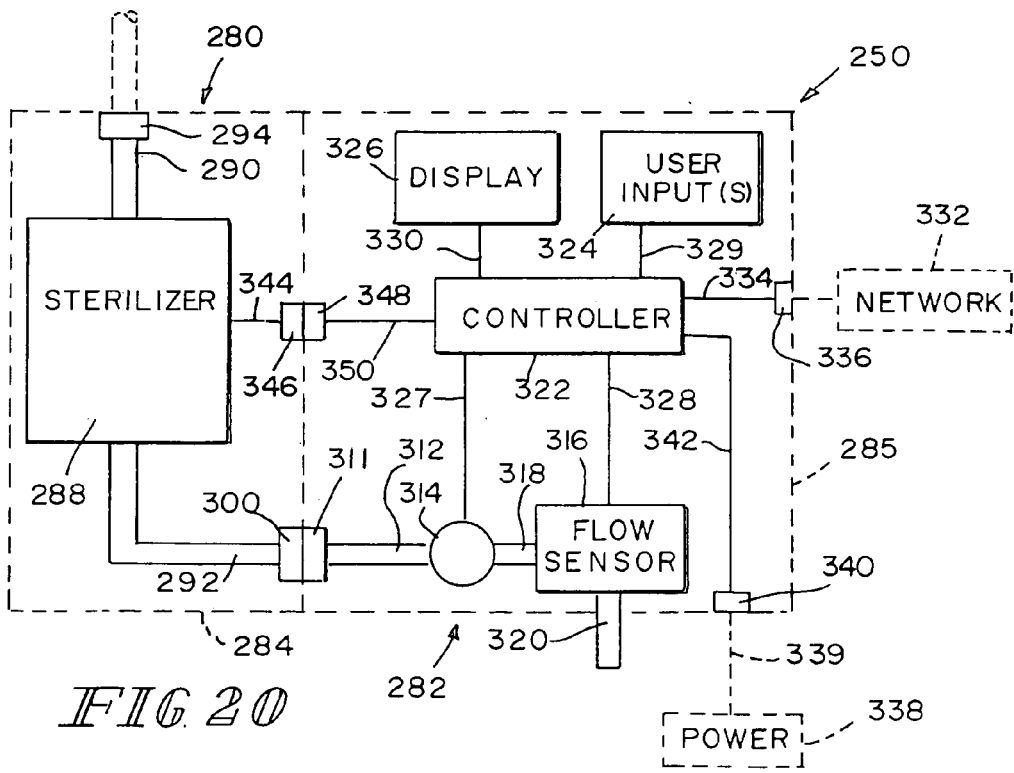
FIG. 20 is a diagrammatic view, similar to FIG. 19, of an alternative water dispenser showing a sterilizer module having a sterilizer and showing a dispenser module having an electric circuit including a controller, the controller being coupled electrically to the sterilizer, and the sterilizer being couplable to an external water line and to a water line of the dispenser module that leads to a control valve of the dispenser module.

Module 280 of FIG. 20 has some of the same components as module 280 of FIGS. 17–19. For example, module 280 of FIG. 20 has inlet line 290, outlet line 292, first coupler 294, and fourth coupler 300. Lines 290, 292 are illustrated diagrammatically in FIG. 20 as coupling directly to sterilizer 288 without the use of any couplers. However, it is within the scope of this disclosure for lines 290, 292 to be coupled to components of sterilizer 288 with suitable couplers. A number of different types of couplers are contemplated by this disclosure. For example, the various couplers of water dispenser 250 may be threaded couplers, quick-connect couplers, barbed couplers, leur lock couplers, cam lock couplers, and the like.

Module 282 of water dispenser 250 has an inlet coupler 311, an inlet line 312, a flow-control valve 314, a flow sensor 316, an intermediate line 318, and an outlet line 320 having an exit nozzle or spigot as shown in FIGS. 19 and 20. Coupler 311 mates with coupler 300 of module 280 so as to form a substantially watertight seal. Line 312 extends from coupler 311 to valve 314. Line 318 extends from valve 314 to flow sensor 316. Line 320 extends from flow sensor 316. The exit nozzle or spigot of line 320 is configured with a leur lock coupler or other suitable coupler that mates with an inlet coupler of a piece of medical equipment to receive water from water dispenser 250. For example, an IV bag 321 is coupleable to the illustrative spigot of line 320 as shown in FIG. 17.

Module 282 comprises an electric circuit having a controller 322, one or more user inputs 324, and a display 326. Controller 322 has a microprocessor, a microcontroller, or other similar logic-based processing component, as well as associated circuit components, such as a clock or oscillator, memory, analog-to-digital converter, parallel-to-serial data converter, and the like. Valve 314 is an electrically actuated valve that is movable between an opened position and a closed position. In some embodiments, valve 314 is a proportional control valve or other such valve having one or more intermediate positions between the opened and closed positions. Thus, valve 314 may include a solenoid, a stepper motor, or any other suitable device having a mechanical portion that moves in response to receiving an electrical signal. In alternative embodiments, valve 314 is operated either manually, pneumatically, or hydraulically.

In the illustrative embodiment of water dispenser 250, user inputs 324 are engaged by a caregiver to control the flow of water from water dispenser 250. In some embodiments, user inputs 324 comprise a momentary input such as a push button, a movable lever, a movable knob, a membrane switch, or the like that is normally biased to a position preventing water from being dispensed and that must be continuously engaged by the caregiver to cause water to be dispensed.

Controller 322 sends a valve-control signal to valve 314 on a line 327 to command valve 314 to move to the opened position, the closed position, or to one of the intermediate positions depending upon an input signal received from user inputs 324 on one or more lines 329. Flow sensor 316 senses the amount of water that is flowing out of line 320 and provides a sensor signal on line 328 to controller 322. Controller 322 conditions the sensor signal, if needed, such as by converting the signal from analog to digital, and processes the sensor signal to determine if valve 314 should be opened further or closed further. In some embodiments, sensor 316 outputs a digital sensor signal. Controller 322 is also configured to process the sensor signal to calculate how much water, in total, flows out of nozzle 320 between opening and closing of valve 314. Thus, illustrative water dispenser 250 has an electronic flow control which comprises one or more of valve 314, sensor 316, controller 322, user input 324, and display 326.

Display 326 is coupled electrically to controller 322 via one or more lines 330 as shown diagrammatically in FIGS. 19 and 20. Display 326 provides various types of visual data to the user regarding the operation or condition of water dispenser 250. Examples of the type of information displayed on display 326 include, the volume of water dispensed (in real time and/or after completion), the volume of water dispensed over some preset period of time (for example, day, week, month), the amount of time elapsed since filter 286 has been changed, the volume of water that has passed through filter 286 since it was last changed, a message that filter 286 needs to be changed, a message that one or more of the components of sterilizer 288 needs to be changed or serviced, various error or alarm messages pertaining to the operation of sterilizer 288, and various error or alarm messages pertaining to the operation of the components, such as valve 314, sensor 316, or controller 322, of the electric circuit of module 282.

Optionally, controller 322 is coupleable to a network 332 of the healthcare facility via a line 334 and coupler 336 as shown diagrammatically in FIGS. 19 and 20. When coupled to network 332, any of the data displayed on display 326 is reported to the network for archiving or for viewing on a remote computer terminal, such as a computer terminal at a nurse station. Error or alarm data communicated to network 332 may be forwarded to maintenance personnel (via e-mail or via computer operated paging) so that corrective action can be taken.

If controller 322 is coupled to network 332 of the healthcare facility and if network 332 includes a nurse tracking system (such as a system in which receivers connected to the network are located throughout the facility and caregiver identification transmitters are carried by caregivers) and/or an equipment status system (such as a remote computer that receives and displays information about the operating conditions and configurations of hospital equipment), such as shown and described, for example, in U.S. Pat. Nos. 6,344, 794; 6,147,592; 5,838,223; 5,699,038; 5,561,412; and RE 35,035, each of which is hereby incorporated herein by reference, then data identifying the caregiver(s) present in a particular room when water dispenser 250 is operated may be correlated with the amount of water dispensed or with other information associated with water dispenser 250 and stored in the memory of remote computer equipment included in network 332.

In some embodiments, controller 322 is configured so that water dispenser 250 will not operate to dispense water unless controller 322 receives data from the nurse tracking system via network 332, or alternatively, a receiver (not shown) included in dispenser 250, indicating that a caregiver carrying or wearing an appropriate transmitter is present in the hospital room in which dispenser 250 is located. Such an arrangement prevents patients from operating dispenser 250 unless a caregiver is present in the patient's room. A similar arrangement where equipment is disabled unless a caregiver having an appropriate transmitter is present in the same room as the equipment, may be employed in connection with any of the equipment coupled to or associated with wall units 212 discussed above in connection with FIGS. 15 and 16.

The components of the electric circuit of module 282 receive electrical power from a power source 338 via a coupler 340 and line a 342. Controller 322 comprises power conditioning circuitry to convert the power from power source 338 (which, in most embodiments, is standard 120 V, 60 Hz AC power) into appropriate voltages (5V or 12V, for example) to operate the various components of the electric circuit, such as valve 314, sensor 316, processor of controller 322, display 326, etc. In the illustrative embodiment, a portion of a power line 339 which extends from power source 338 is routed through lower chase 268 and terminates at a coupler 341, shown in FIG. 18, that mates automatically with coupler 340 when module 282 is inserted into cavity 254 of headwall unit 260.

In some embodiments sterilizer 288 has its own electric circuit including a line 344 and a coupler 346 as shown diagrammatically in FIG. 20. In such embodiments, the electric circuit of module 282 has a coupler 348 and a line 350 that extends between coupler 350 and controller 322. Controller 322 provides power to sterilizer 288 and exchanges data with sterilizer 288 via lines 344, 350 and couplers 346, 348. When controller 322 is coupled to the electric circuit of sterilizer 288, various types of operating data, error conditions, alarm conditions, and the like relating to sterilizer 288 are displayable on display 326 and are communicated to network 332. In some embodiments, controller 322 is programmed to operate and control the components of sterilizer 288, and in other embodiments, sterilizer 288 has its own controller that is programmed to control and operate the components of sterilizer 288.

The word "line" in this disclosure, including in the claims, is used broadly to refer to, for example, water lines 290, 292, 312, 318 (if water flows through the lines) and electrical lines 327, 328, 329, 330, 334, 342, 344, 350 (if electrical signals or power is associated with the lines). It will be appreciated that electrical lines 327, 328, 329, 330, 342 may each comprise multiple conductors or wires. For example, lines 330, 334, 344, 350 may comprise an 8-bit, 16-bit, 32-bit, etc. data transfer bus and line 342 may comprise a ground wire, a positive voltage wire, and a negative voltage wire. Water lines 290, 292, 312, 318 may comprise pipes, tubes, hoses, passages in valves, passages in manifolds, and the like.

Housings 284, 285 of modules 280, 282, respectively, are configured to fit into cavity 254 of headwall unit 260. Headwall unit 260 comprises a horizontally extending panel 352, a portion of which underlies cavity 254 as shown in FIG. 18. Headwall unit 260 further comprises a pair of vertically extending side panels 354 lying alongside cavity 254. Housings 284, 285 each have a pair of spaced apart side panels or walls 356 that, in the illustrative embodiment, are substantially planar and extend vertically.

When housings 284, 285 are received in cavity 254, the side walls 356 at the interface between housings 284, 285 are positioned to lie alongside one another so that coupler 300 of module 280 mates with coupler 311 of module 282 thereby establishing fluid communication between lines 292, 312 through couplers 300, 311. In addition, when housings 284, 285 are received in cavity 254, the other side walls 356 of housings 284, 285 are positioned to lie alongside respective side panels 354 of headwall unit 260. Housings 284, 285 each have a bottom panel or wall 360 that rests upon panel 352 of headwall unit 260. Coupler 340 associated with bottom wall 360 of housing 285 mates automatically with coupler 341 associated with panel 352 when housings 284, 285 are received in cavity 254.

Illustrative housing 285 has a front panel or wall 358 that is substantially coplanar with front panel 310 of housing 284 when housings 284, 285 are received in cavity 254. In addition, front panels 310, 358 of housings 284, 285, respectively, are substantially coplanar with front panels 362 of upper chase 266 of headwall unit 260 when housings 284, 285 are received in cavity 254. Furthermore, each of housings 284, 285 has a top wall 364, an upper chamfer wall 366, and a lower chamfer wall 368 which are substantially coplanar with top panels 370, upper chamfer panels 372, and lower chamfer panels 374, respectively, of headwall unit 260. Thus, housings 284, 285 are configured to match the shape or contour of the outer surface of upper chase 266. Suitable locking mechanisms (not shown), such as tabs, posts, pins, slots, latches, hooks, fingers, catches, and the like, as well as combinations of these, are provided in some embodiments to retain water dispenser 250 in cavity 254.

In alternative embodiments, water dispenser 250 has more modules than illustrative modules 280, 282. For example, embodiments having multiple sterilizer modules, including separate modules with ultraviolet lights, chemical treatment equipment, heat exchangers, and the like, are contemplated by this disclosure. In such embodiments, the size of cavity 254 of headwall unit 260 is modified appropriately to receive how ever many modules are included in dispenser 250. It is also within the scope of this disclosure for filtering or sterilizing components to be housed in the interior regions of upper chase 266 or lower chase 268 or both. In addition, it within the scope of this disclosure for dispenser module 282 to be the only module coupled to headwall unit 260 and for the filter or sterilizer equipment to be located remotely in the healthcare facility such that filtered and/or sterilized water is piped through the healthcare facility to dispenser module 282.

In alternative embodiments, lower chase 268 is configured with its own cavity, similar to cavity 254, for receiving a portion or all of water dispenser 250. Furthermore, other configurations of cavities for receiving the various water dispensers disclosed herein are within the scope of this disclosure. Such alternative cavities include, for example, cavities having closed tops with top panel 370 bridging over the underlying cavity, for example. In some embodiments of wall units 212 having water dispensers, some of the filtering or sterilizing components are housed in the interior regions of wall units 212 and are inaccessible without removing, for example, one or both of panels 229.

Although the invention has been described in detail with reference to certain preferred embodiments, variations and modifications exist within the scope and spirit of the invention as described and defined in the following claims.

The invention claimed is:

1. A modular wall unit for use in constructing a room in a healthcare facility, the modular wall unit comprising
   a pair of spaced apart sides,
   a service-delivery component supported between the pair of spaced apart sides
   a first panel movable vertically relative to the pair of spaced apart sides between a first position blocking access to the service-delivery component and a second position allowing access to the service-delivery component,
   a second panel that moves vertically relative to the pair of spaced apart, and
   a linkage mechanism interconnecting the first panel and the second panel, the linkage mechanism being configured such that upward movement of the first panel results in downward movement of the second panel and such that downward movement of the first panel results in upward movement of the second panel.

2. The modular wall unit of claim 1, wherein at least one of the sides has an opening through which a service-delivery line is routed to the service-delivery component.

3. The modular wall unit of claim 1, wherein the service-delivery component is a gas outlet.

4. The modular wall unit of claim 3, further comprising a gas flow meter coupled to the gas outlet and situated between the pair of spaced apart sides.

5. The modular wall unit of claim 1, further comprising a data monitor situated between the pair of spaced apart sides.

6. The modular wall unit of claim 5, wherein the first panel blocks access to the data monitor when the first panel is in the first position and the data monitor is accessible when the first panel is in the second position.

7. The modular wall unit of claim 1, further comprising an environmental control panel situated between the pair of spaced apart sides.

8. The modular wall unit of claim 7, wherein the first panel blocks access to the environmental control panel when the first panel is in the first position and the environmental control panel is accessible when the first panel is in the second position.

9. The modular wall unit of claim 1, further comprising a water dispenser situated between the pair of spaced apart sides.

10. The modular wall unit of claim 9, wherein the first panel blocks access to the water dispenser when the first panel is in the first position and the water dispenser is accessible when the first panel is in the second position.

11. The modular wall unit of claim 1, wherein the first panel moves upwardly when moving from the first position to the second position.

12. The modular wall unit of claim 1, wherein the first panel moves downwardly when moving from the first position to the second position.

13. The modular wall unit of claim 1, further comprising user inputs that are usable to adjust room lighting, the first panel blocks access to the user inputs when the first panel is in the first position, and the user inputs are accessible when the first panel is in the second position.

14. The modular wall unit of claim 1, further comprising user inputs that are usable to adjust room temperature, the first panel blocks access to the user inputs when the first panel is in the first position, and the user inputs are accessible when the first panel is in the second position.

15. The modular wall unit of claim 1, further comprising user inputs that are usable to control entertainment equipment, the first panel blocks access to the user inputs when the first panel is in the first position, and the user inputs are accessible when the first panel is in the second position.

16. The modular wall unit of claim 1, further comprising tracks and the first panel having side edges that are received in the tracks.

17. The modular wall unit of claim 1, wherein the second panel is situated beneath the first panel.

18. The modular wall unit of claim 1, further comprising a locking mechanism to lock the first panel in at least one of the first and second positions.

* * * * *